United States Patent [19]

Eiermann et al.

[11] Patent Number: 5,866,732

[45] Date of Patent: Feb. 2, 1999

US005866732A

[54] PREPARATION OF ALKYL BROMIDES FROM AQUEOUS HYDROBROMIC ACID AND OLEFINS

[75] Inventors: Matthias Eiermann, Limburgerhof; Klaus Ebel, Lampertheim, both of Germany

[73] Assignee: BASF Aktiengesellschaft, Ludwigshafen, Germany

[21] Appl. No.: 916,351

[22] Filed: Aug. 22, 1997

[30]     Foreign Application Priority Data

Aug. 28, 1996 [DE] Germany ............... 196 34 818.8

[51] Int. Cl.⁶ ............... C07C 21/00; C07C 17/08
[52] U.S. Cl. ............... 570/248; 570/246; 570/250
[58] Field of Search ................... 570/246, 248, 570/250

[56]         References Cited

U.S. PATENT DOCUMENTS 3,400,162  9/1968  Beets .
3,679,759  7/1972  Schmerling ............... 570/246

FOREIGN PATENT DOCUMENTS 825 477    6/1979  Russian Federation .
1020853    2/1966  United Kingdom .

OTHER PUBLICATIONS

Sherril et al., *J. Am. Chem. Soc.*, vol. 56, (1934), pp. 926–930.

Landini et al., *J. Org. Chem.*, vol. 45, (1980), pp. 3527–3529.

Carothers et al., *J. Amer. Chem. Soc.*, vol. 55, (1933) pp. 786–788.

*Primary Examiner*—Alan Siegel
*Attorney, Agent, or Firm*—Keil & Weinkauf

[57]         ABSTRACT

Alkyl bromides are prepared from mixtures comprising aqueous hydrobromic acid and olefins in a process in which there is concentration of the aqueous hydrobromic acid present during the reaction.

10 Claims, No Drawings

PREPARATION OF ALKYL BROMIDES FROM AQUEOUS HYDROBROMIC ACID AND OLEFINS

Alkyl bromides are very important for a large number of applications in organic chemistry, for example for organometallic reactions. It is generally known to prepare them from the corresponding alcohols by reaction with thionyl bromide or hydrobromic acid. Alkyl bromides can also be obtained by adding HBr onto olefins; this entails use of gaseous hydrogen bromide in a non-aqueous medium such as glacial acetic acid. The reaction rate for the addition is increased by using Lewis acids, such as iron(III) salts, as catalysts in the reaction of the gas (cf. Houben-Weyl, Vol. V/4). However, gaseous hydrogen bromide is costly and not available in unlimited amounts on the industrial scale.

J. Am. Chem. Soc. 56 (1934) 926 (M. L. Sherrill, K. E. Mayer, G. F. Walker) discloses that the addition of hydrobromic acid in concentrated aqueous solution onto olefins such as 1-pentene or 1-heptene takes place very slowly. The reaction requires large excesses of hydrobromic acid so that this synthesis has no economic importance.

It is possible by adding onium salts (D. Landini et al., J. Org. Chem. 45 (1980) 3527), free-radical initiators (cf. NL-A 65 03537) or stoichiometric amounts of phosphorus tribromide (SU-A 825 477) to improve the reaction rate and increase the yield. However, the reagents required are costly and, in the case of the free-radical initiators, result in isomeric products in the case of nonsymmetrically substituted olefins. U.S. Pat. No. 3,679,759 discloses carrying out the reaction under pressure to increase the yield. However, this requires elaborate pressure equipment.

Rapid reactions have hitherto been observed only in the case of highly reactive conjugated dienes and enynes, and these are the starting point for preparative processes [W. H. Carothers et al., J. Am. Chem. Soc. 55, (1933) 787].

It is an object of the present invention to improve the preparation of alkyl bromides from aqueous hydrobromic acid and olefins. It is particularly intended to simplify the process and reduce the costs.

We have found that this object is achieved by a process for preparing alkyl bromides from mixtures comprising aqueous hydrobromic acid and olefins in which there is concentration of the hydrobromic acid present during the reaction.

This concentration takes place in an advantageous manner by distilling water out during the reaction, in particular by removing the water in the form of an azeotrope with an organic component which is present in the reaction mixture and is subsequently returned to the reaction mixture.

The dependent claims relate to further preferred embodiments of the invention.

The concentration according to the invention of the hydrobromic acid present makes it possible to choose a more favorable ratio of the starting materials, so that it is also possible to employ the aqueous hydrobromic acid which is easily available at favorable cost on the industrial scale for synthesizing alkyl bromides starting from olefins. Another advantage is that the added acid is completely consumed by the end of the reaction and the remaining water is, in some circumstances with traces of HBr, distilled out. This makes it possible for the subsequent workup of the alkyl bromide which is formed in the reaction to be straightforward, by direct distillation without previous phase separation and/or extraction steps.

It is possible according to the invention to concentrate the hydrobromic acid by distilling out the water on its own. However, it is preferred to remove the water in the form of an azeotrope with an organic component which is present in the reaction mixture. The component which forms an azeotrope with water is preferably cyclopentane, cyclohexane, benzene or toluene. It is possible and advantageous for it to be continuously separated out of the distillate by phase separation and returned to the reaction mixture. It is very particularly advantageous for the component which forms an azeotrope with water to be the alkyl bromide, ie. the reaction product. In this case, phase separation in the distillate results in a product which is already substantially purified.

The addition of the initial components to the reaction mixture can take place either by adding the olefin to the hydrobromic acid or, conversely, adding the hydrobromic acid to the olefin. If one or more solvents are used, these can likewise either be initially present or else added to the other reactants.

During the reaction, it is advantageous for the mixture to be mixed, preferably by using a mechanical stirrer.

The reaction takes place under an absolute pressure of from 0.001 to 1000, preferably from 0.1 to 10, bar. The reaction is particularly preferably carried out under atmospheric pressure. The reaction temperature is from $-50°$ to $400°$ C., preferably from $-20°$ to $150°$ C. The reaction temperature is particularly advantageously from $0°$ C. to the boiling point of the particular mixture under atmospheric pressure because the process can then be carried out particularly straightforwardly.

The hydrobromic acid is employed as aqueous solution with a concentration in the range from 0.1 to 95% by weight, in particular 1 to 80% by weight, preferably from 40 to 65% by weight.

The olefin or the mixture of olefins to be reacted can be reacted with the aqueous hydrobromic acid alone or in the presence of one or more solvents. These solvents can be immiscible or else miscible; however, the reaction is preferably carried out without solvent or in the presence of an alkane or mixture of alkanes, such as, in particular, cyclopentane, cyclohexane or mixtures of isomeric (cyclo) pentanes or (cyclo)hexanes.

The olefin or mixture of olefins employed in the reaction has the general formula $R^1(R^2)C=C(R^3)R^4$ where $R^1$, $R^2$, $R^3$ and/or $R^4$ are each hydrogen, deuterium or a $C_1$–$C_{200}$-alkyl, $C_3$–$C_{200}$-cycloalkyl, $C_2$–$C_{200}$-alkenyl, $C_3$–$C_{200}$-cycloalkenyl or $C_6$–$C_{200}$-aryl radical which is unsubstituted or substituted by functional groups. Said functional group is chemically inert under the reaction conditions. It is preferably an aryl, halide or nitro radical. In addition, $R^1$, $R^2$, $R^3$ and/or $R^4$ can also be parts of conjoint rings, in particular of $C_1$–$C_{200}$-alkylene, $C_3$–$C_{200}$-cycloalkylene, $C_2$–$C_{200}$-alkenylene, $C_3$–$C_{200}$-cycloalkenylene or $C_6$–$C_{200}$-arylene groups. $C_1$–$C_5$-alkylene groups are preferred, in particular $C_3$–$C_4$-alkylene radicals. It is furthermore possible for $R^1$ with omission of $R^2$, and $R^3$ with omission of $R^4$, to be double-bonded, ie. in this case to be $C_1$–$C_{200}$alkylidene, $C_3$–$C_{200}$-cycloalkylidene, $C_2$–$C_{200}$-alkenylidene, $C_3$–$C_{200}$-cycloalkenylidene or $C_6$–$C_{200}$-arylidene groups.

The reaction can be carried out with the pure olefin or else with a mixture of various olefins as produced, for example, in the steam cracking of long-chain hydrocarbons, in elimination reactions on, for example, alcohol mixtures, in pyrolyses of hydrocarbons, in the dehydrogenation of alkanes or hydrogenation of alkynes, or in Wittig or Wittig-Horner reactions.

The reaction can be carried out in the absence or presence of a suitable catalyst. Catalysts which can be used are any elements M or compounds, for example salts, coordination compounds, complex compounds, of the general formula $M_wL_xA_y(H_2O)_z$ or mixtures and alloys thereof, where M is one or more elements of groups IA, IIA, IIIB, IVB, VB, VIB, VIIB, VIII, IB, IIB, IIIA or IVA of the Periodic Table and the lanthanides, preferably one or more elements of groups IIA, VB, VIB, VIIB, VIII, IB, IIB and IIIA of the Periodic Table, particularly preferably iron, zinc or aluminum, L is a uni- or multidentate ligand or a combination of different uni- or multidentate ligands such as carboxylates, cyanide, halide, amine, amide, phosphine, phosphonate, nitrate, nitrite, alcoholate, sulfide, thiolate, sulfonate, olefin, aryl, nitrile, imine or carbonyl, A is one or more elements or one or more compounds of elements of groups VB, VIB, IIIA, IVA, VA, VIA or VIIA of the Periodic Table, preferably a borate, carboxylate, carbonate, cyanide, amide, nitrate, nitrite, phosphate, phosphonate, polyphosphate, heteropolyphosphate of molybdenum or tungsten, oxide, hydroxide, alcoholate, sulfide, sulfate, thiolate, sulfinate, sulfonate, selenide, halide, halate or perhalate, very particularly preferably bromide or hydroxide, w is at least 1, x is greater than or equal to zero, y is at least 1, z is greater than or equal to zero.

The catalyst can be employed in pure form, in solution or else on a carrier material. Carriers which can be employed are organic resins such as iron exchanger resins, molecular sieves such as montmorillonites, kaolinites or bentonites or else zeolites, porous materials composed of carbon such as active carbon, and oxides, sulfates, sulfides, hydroxides, halides, phosphates or pyrophosphates of elements of groups IA, IIA, IIIB, IVB, VIB, VIIB, VIII, IB, IIB, IIIA or IVA of the Periodic Table, and the lanthanides. Use in pure form is preferred. The pure catalyst or one supported in this way can be used either as powder, as chips or as shaped articles such as in extrudates.

The olefin:HBr molar ratio is, as a rule, from 0.001:1 to 1000:1, preferably 0.1:1 to 10:1 and particularly preferably 0.2:1 to 5:1.

The molar ratio of the catalyst employed to the olefin employed can be from 0.001 to 1000, preferably from 0.01 to 10 and particularly preferably from 0.1 to 1 mol %.

The workup following the reaction can take place in a variety of conventional ways. However, the reaction mixture is preferably worked up by direct distillation of the product without previous workup steps.

Examples are given of the process according to the invention hereinafter:

EXAMPLES

Example 1

136 g of cyclopentene, 180 g of cyclopentane, 310 g of 47% strength aqueous HBr and 2.7 g of zinc bromide were refluxed in a stirred apparatus with water trap until no further aqueous phase was formed in the water trap. The cyclopentene conversion was 90% of theory (GC, FID areas), and the selectivity for cyclopentyl bromide was 99% in each case. Workup took place by distillation under reduced pressure to result, for example, in about 220 g of pure cyclopentyl bromide from the stated mixture.

Example 2

The process was as in Example 1 but 4.8 g of iron(III) sulfate were used in place of 2.7 g of zinc bromide. The cyclopentene conversion after removal of water was complete was 98% of theory (GC, FID areas), and the selectivity was 99%.

Example 3

The process was as in Example 1 but 4.1 g of aluminum sulfate were used in place of 2.7 g of zinc bromide. The cyclopentene conversion after removal of water was complete was 90% of theory (GC, FID areas), and the selectivity was 99%.

Example 4

The process was as in Example 1 but 164 g of cyclohexene and 168 g of cyclohexane were used in place of 136 g of cyclopentene and 180 g of cyclopentane. The cyclohexene conversion after removal of water was complete was 98% of theory (GC, FID areas), and the selectivity was 99%. 250 g of pure cyclohexyl bromide were obtained in this way from the stated mixture.

We claim:

1. A process for preparing alkyl bromides, which process comprises mixing aqueous hydrobromic acid and an olefin and reacting the aqueous hydrobromic acid and the olefin while maintaining the concentration of the aqueous hydrobromic acid substantially constant during the reaction.

2. A process as claimed in claim 1, wherein maintaining the concentration of the aqueous hydrobromic acid substantially constant during the reaction is effected by distilling out water or an azeotrope of water from the reaction mixture of aqueous hydrobromic acid and olefin.

3. A process as claimed in claim 1, wherein the reaction is carried out under an absolute pressure of from 0.1 to 10 bar.

4. A process as claimed in claim 1, wherein the reaction is carried out at from −20° to 150° C.

5. A process as claimed in claim 1, wherein the aqueous hydrobromic acid is employed in a concentration of from 1 to 80% by weight.

6. A process as claimed in claim 1, wherein an olefin of the formula $R^1(R^2)C=C(R^3)R^4$ where $R^1$, $R^2$, $R^3$ or $R^4$ are each, independently of one another, hydrogen, deuterium or a $C_1$–$C_{200}$-alkyl, $C_3$–$C_{200}$-cycloalkyl, $C_2$–$C_{200}$-alkenyl, $C_3$–$C_{200}$-cycloalkenyl or $C_6$–$C_{200}$-aryl radical which is unsubstituted or substituted by functional groups, or wherein $R^1$ with omission of $R^2$, and $R^3$ with omission of $R^4$, are doubly bonded as $C_1$–$C_{200}$-alkylidene, $C_3$–$C_{200}$-cycloalkylidene, $C_2$–$C_{200}$-alkenylidene, $C_3$–$C_{200}$-cycloalkenylidene or $C_6$–$C_{200}$-arylidene is employed.

7. A process as claimed in claim 1, wherein cyclopentene, pure or mixed with $C_1$–$C_{10}$-olefins, is used as olefin.

8. A process as claimed in claim 1, wherein a mixture of hydrocarbons which consists of more than 50% $C_1$–$C_{10}$-hydrocarbons and forms an azeotrope with water under the reaction conditions is used as solvent in the reaction.

9. A process as claimed in claim 8, wherein the molar ratio of cyclopentene to HBr is from 2:1 to 0.2:1.

10. A process as claimed in claim 1, wherein a catalyst is additionally present in the reaction mixture and comprises one or more compounds of the general formula $M_wL_xA_y(H_2O)_z$, where M is one or more elements of groups IA, IIA, IIIB, IVB, VB, VIB, VIIB, VIII, IB, IIB, IIIA or IVA of the Periodic Table or the lanthanides, preferably M is iron, zinc and/or aluminum, L is a uni- or multidentate ligand or a combination of various uni- or multidentate ligands, in particular of carboxylates, cyanides, halides, amines, amides, phosphines, phosphonates, nitrates, nitrites, alcoholates, sulfides, thiolates, sulfonates, olefins, aryls, nitriles, imines or carbonyl, A is one or more elements or compounds of elements of groups VB, VIB, IIIA, IVA, VA, VIA or VIIA of the Periodic Table, preferably one or more compounds selected from the group of borate, carboxylate, carbonate, cyanide, amide, nitrate, nitrite, phosphate, phosphonate, polyphosphate, heteropolyphosphate of molybdenum or tungsten, oxide, hydroxide, alcoholate, sulfide, sulfate, thiolate, sulfonate, sulfinate, selenide, halide, halate and perhalate, more preferably selected from bromide and hydroxide, and w is at least 1, x is greater than or equal to zero, y is at least 1, and z is greater than or equal to zero.

* * * * *